United States Patent [19]

Muller et al.

[11] 4,334,974
[45] Jun. 15, 1982

[54] ELECTROCHEMICAL OXYGEN SENSOR, PARTICULARLY FOR USE WITH EXHAUST GASES OF INTERNAL COMBUSTION ENGINES, AND ESPECIALLY FOR POLAROGRAPHIC APPLICATION

[75] Inventors: Klaus Muller, Tramm; Helmut Maurer, Schwieberdingen; Ernst Linder, Mühlacker; Franz Rieger, Aalen; Karl H. Friese, Leonberg; Harald Reber; Hermann Dietz, both of Gerlingen; Hermann Ziener, Möglingen; Friedrich Esper, Leonberg; Gerhard Holfelder, Ditzingen, all of Fed. Rep. of Germany

[73] Assignee: Robert Bosch GmbH, Stuttgart, Fed. Rep. of Germany

[21] Appl. No.: 121,598

[22] Filed: Feb. 14, 1980

[30] Foreign Application Priority Data

Feb. 23, 1979 [DE] Fed. Rep. of Germany ....... 2907032

[51] Int. Cl.$^3$ ............................................. G01N 27/58
[52] U.S. Cl. ................................................ 204/195 S
[58] Field of Search ............................ 204/1 S, 195 S

[56] References Cited

U.S. PATENT DOCUMENTS

| | | | |
|---|---|---|---|
| 3,691,023 | 9/1972 | Ruka et al. | 204/1 T |
| 3,989,614 | 11/1976 | Tien | 204/195 S |
| 4,107,019 | 8/1978 | Takao et al. | 204/195 S |
| 4,119,513 | 10/1978 | Shum et al. | 204/195 S |
| 4,155,827 | 5/1979 | Maurer et al. | 204/195 S |
| 4,157,282 | 6/1979 | Riddel | 204/1 S |
| 4,157,948 | 6/1979 | Maurer | 204/1 S |

FOREIGN PATENT DOCUMENTS 2711880 9/1978 Fed. Rep. of Germany ... 204/195 S
2718907 11/1978 Fed. Rep. of Germany ... 204/195 S Primary Examiner—G. L. Kaplan
Attorney, Agent, or Firm—Frishauf, Holtz, Goodman & Woodward

[57] ABSTRACT

To permit a layer construction, which is inexpensive and lends itself to mass production manufacture, a solid electrolyte body, in plate-like construction, with electrodes at either thereof is positioned in a housing with a portion thereof extending in the region where it is exposed to gases to be sensed; a porous cover is applied on one of the electrodes, the porous cover having a predetermined diffusion resistance to oxygen molecules. A flat insulating plate of approximately the same dimension as the solid electrolyte plate is positioned flat thereagainst, and a flat layer-like electrical heating element is secured on the flat insulating plate or, in other embodiments, against another insulating covering on the other side of the heating element as well, close to the electrodes and adjacent the plane surfaces of the body. The heating element and the electrodes of the sensing element are carried out as conductive tracks for connection to respective sources of operating or biassing potential and, with respect to the sensing electrodes, to an evaluation circuit.

14 Claims, 9 Drawing Figures

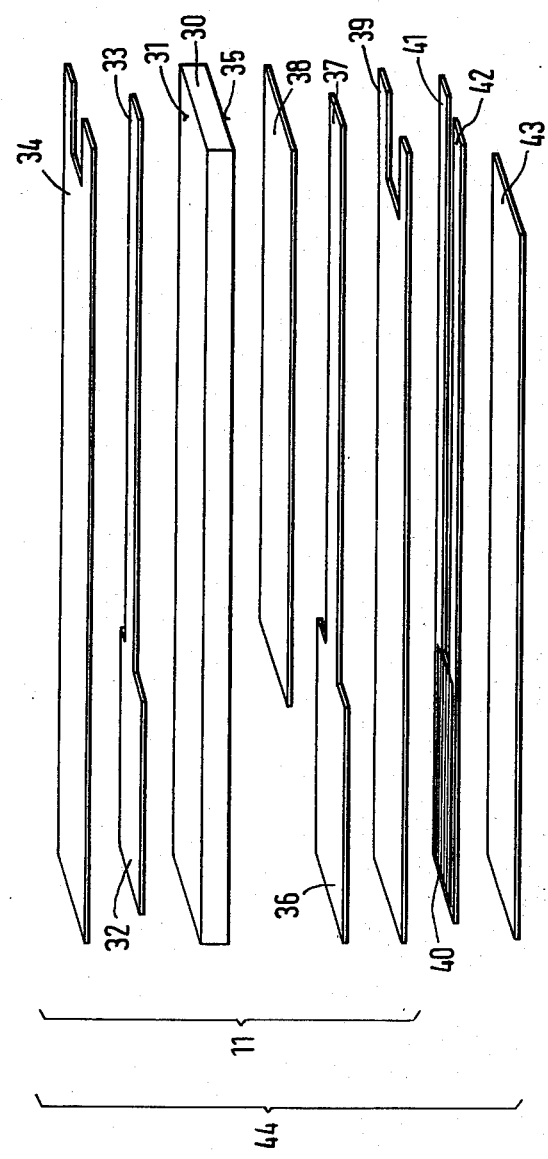

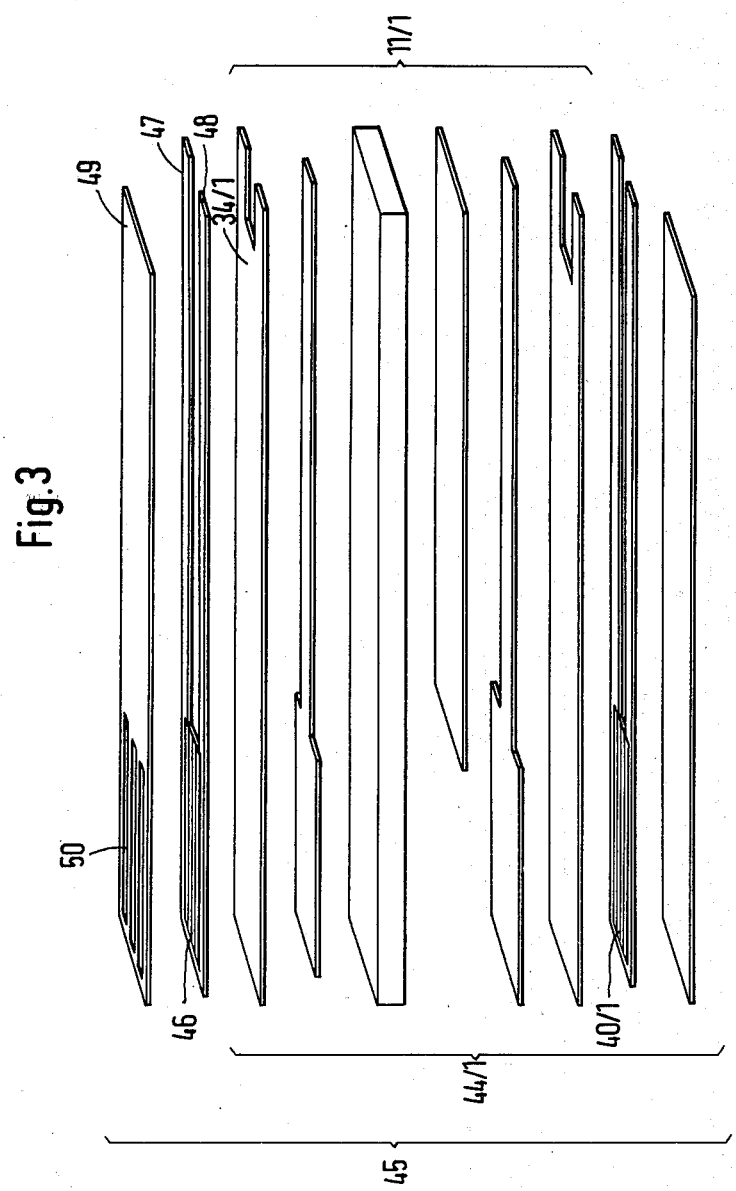

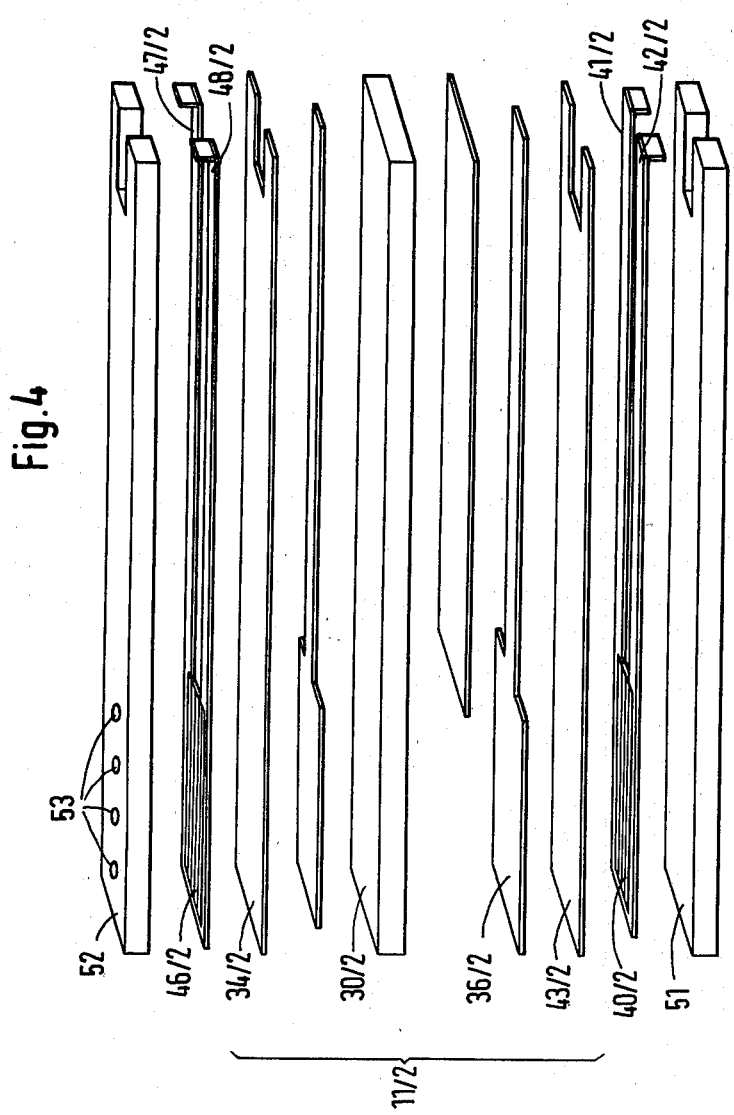

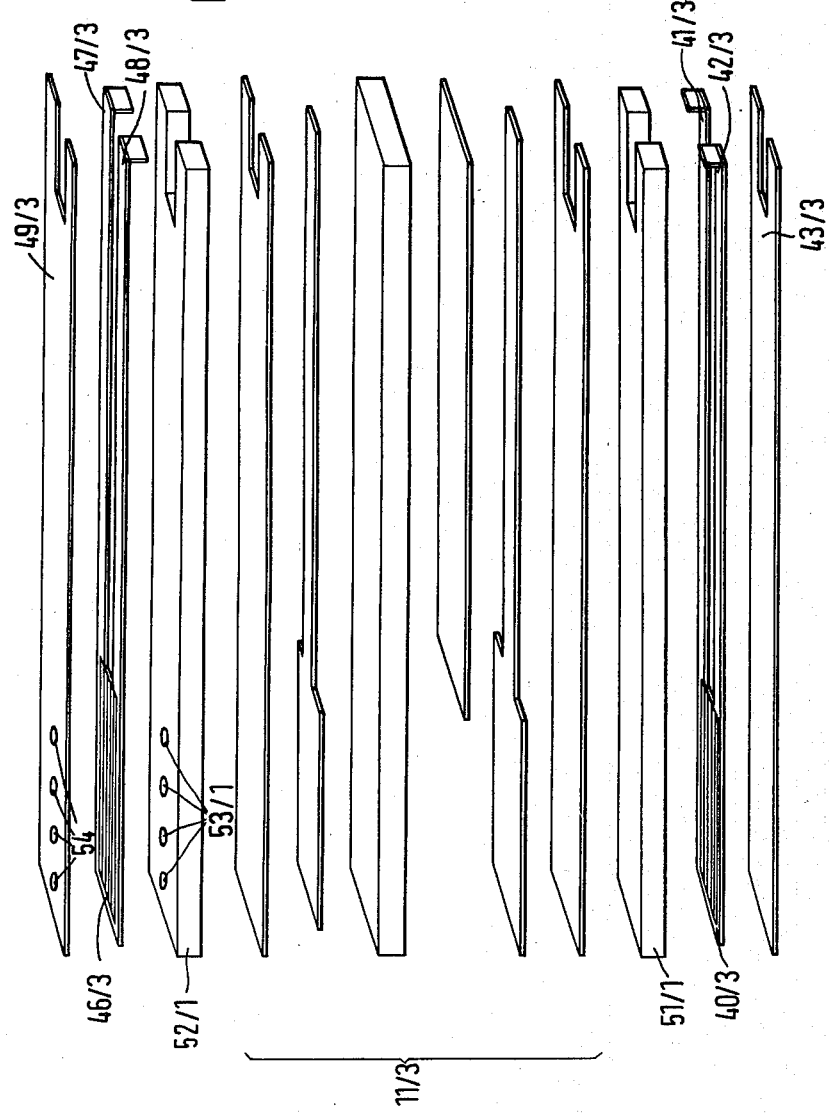

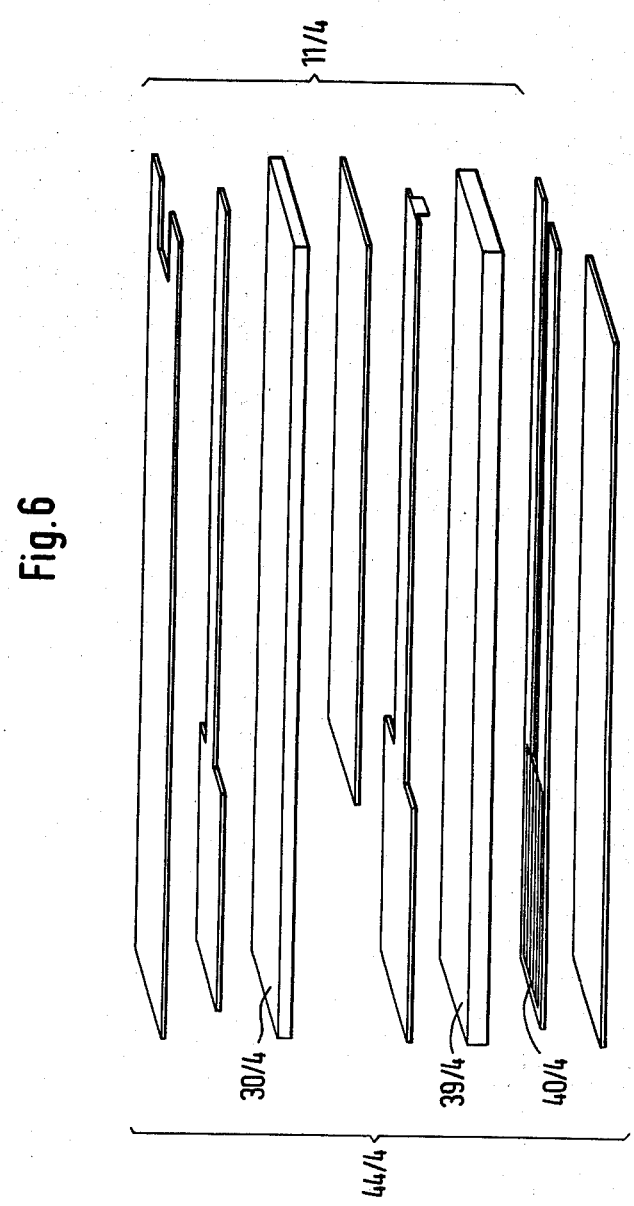

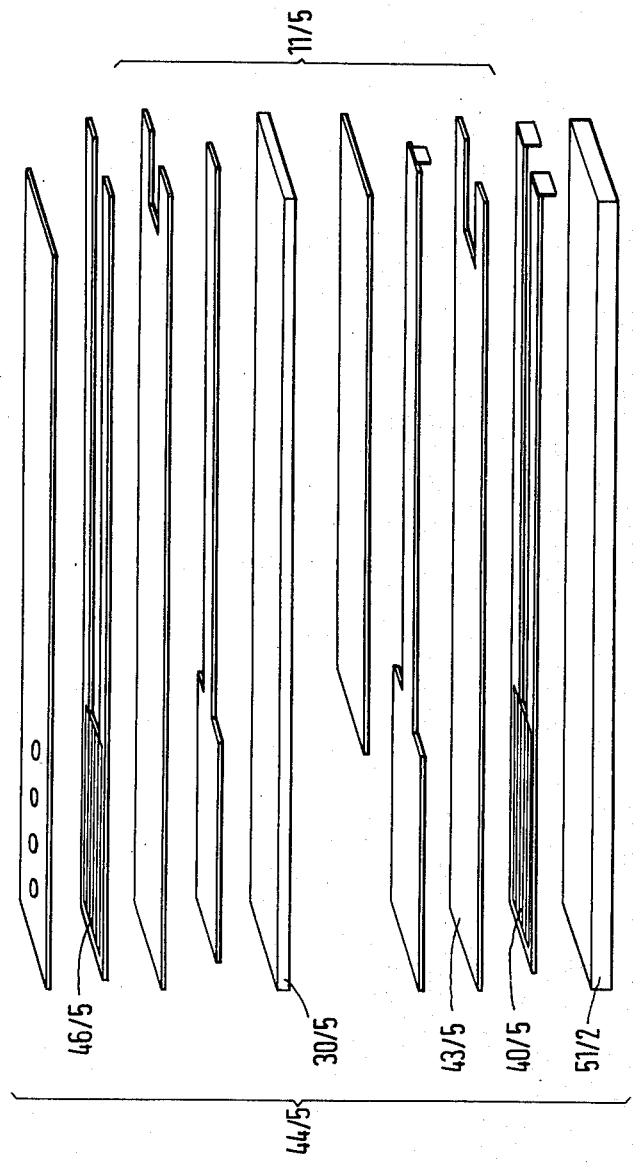

ELECTROCHEMICAL OXYGEN SENSOR, PARTICULARLY FOR USE WITH EXHAUST GASES OF INTERNAL COMBUSTION ENGINES, AND ESPECIALLY FOR POLAROGRAPHIC APPLICATION

Reference to related publications and patents:
U.S. Pat. No. 4,157,208;
U.S. Pat. No. 3,691,023, Ruka et al.;
U.S. Pat. No. 6,093, filed Jan. 24, 1979, CIP of Ser. No. 885,368, filed Mar. 13, 1978, Dietz, now abandoned, based on now published German patent disclosure document DE-OS No. 27 11 880 assigned to the assignee of this application;
U.S. Ser. No. 121,599, filed Feb. 14, 1980, Maurer; now U.S. Pat. No. 4,300,990, assigned to the assignee of this application.

The present invention relates to an electrochemical sensor, and more particularly to a sensor to determine the oxygen content of gases occurring in combustion processes, and especially exhaust gases from internal combustion engines. The invention is particularly applicable to polarographic sensors, that is, sensors which have a voltage applied thereto and in which the oxygen content is measured and forms an analog of current flowing through the sensor upon application of the bias voltage, the intensity of current being evaluated to provide an output signal representative of the oxygen content in the gases to which the sensor is exposed.

BACKGROUND OF THE PRIOR ART

Various types of sensors have been known and one such sensor is described, for example, in U.S. Pat. No. 4,157,282, Riddel. This sensor has a plate-like solid electrolyte body, on the opposite major sides of which electrodes are applied which are exposed to the gas to be tested or analyzed. A voltage signal is provided by the electrodes which depends on the oxygen content of the gas. This type of sensor is referred to as a potentiometric sensor since the sensor element itself provides an output voltage in dependence on the oxygen content of the gases. U.S. Pat. No. 3,691,023, Ruka et al., describes a sensor which likewise uses a plate-like solid electrolyte body on which electrodes are applied to the major surfaces, and located transverse to the stream of gas to be tested. A voltage is applied to the electrodes of this sensor. The current flowing to the sensor will be dependent on the oxygen of the gas. The current will be limited by gaseous diffusion. This sensor is referred to as a polarographic sensor. It is supplied with a heating element to set a certain and predetermined working temperature in order to heat the solid electrolyte body to its operating temperature. Another type of sensor is described in U.S. application Ser. No. 006,093, filed Jan. 24, 1979, now abandoned, Dietz, based on German Disclosure Document DE OS No. 27 11 880, in which the sensing electrode is covered with a porous coating to form a diffusion barrier for the oxygen molecules of a test gas. This sensor is of tubular shape, closed off at one end, and utilizes a reference gas, for example the oxygen of ambient air, which is supplied to the interior of the closed tube.

THE INVENTION

It is an object to improve an oxygen sensor, of the polarographic type having a plate-like electrode, so that it can be manufactured under mass production conditions with high reliability and inexpensively, and in which the heating arrangement for the sensor is so constructed that it has short response time, while being suitable for operation under the difficult environmental conditions encountered in automotive use.

Briefly, the plate-like solid electrolyte body, for example zirconium dioxide, having on both major surfaces electrodes and their leads applied thereto, is supplied with a porous cover on one of the electrodes. The cover has a predetermined diffusion resistance to oxygen molecules. A flat insulating plate having at least approximately the same dimensions as the solid electrolyte body is positioned flat thereagainst. The flat insulating plate has a layer-like electrical heating element secured to one of the flat surfaces, and positioned close to the electrodes on the solid electrolyte body, adjacent the plane surfaces thereof. Means are provided to apply an electrical voltage to the electrodes, for example by extending the resistance electrodes lengthwise to terminal contacts, for connection to a battery to provide heating power to the flat electrodes, the electrodes on the solid electrolyte body, themselves, being connected to a source of bias voltage so that the current flow, upon changing oxygen conditions, will be a measure of the oxygen content in the gases.

The sensor has the advantage over prior art structures that it can be easily made under mass production conditions at low price. A polarographic sensor with built-in heating is provided which, due to the low heat capacity of parallel plates applied closely against each other, has short response time while still capable of reliable operation under the difficult environmental conditions when applied to sense the oxygen content of exhaust gases from automotive engines.

In accordance with a preferred feature of the invention, the porous cover is a plate-like element formed as a pressed plate, which permits reliable and reproducible determination of the porosity to oxygen molecules, and ease of assembly of the overall structure. Forming the porous cover as a press element is an excellent solution for the sensor by readily determining and defining the porosity of the cover which serves as a diffusion barrier.

Drawings, illustrating various examples:

FIG. 2 is an exploded view of the sensor element itself showing a plate-like solid electrolyte body as the carrier of the sensor element with a heating element applied thereagainst;

FIG. 3 is an exploded view similar to FIG. 2 of another embodiment of the sensor element, to which a second heating element has been additionally added;

FIG. 4 is an exploded view similar to FIG. 2 of a third embodiment in which the major surfaces of the solid electrolyte body have a flat insulator applied thereto which has a heater element facing the solid electrolyte body, with insulating plates interposed;

FIG. 5 is an exploded view of a fourth embodiment of the sensor element which is similar to FIG. 4, but in which the heater elements are applied at the surface remote from that facing the solid electrolyte body;

FIG. 6 is an exploded view of a fifth embodiment in which a plate-like insulator is utilized as a carrier body and the sensor element and the heating elements are integrated together;

FIG. 7 is an exploded view of a sixth embodiment of a sensor in which an electric insulator located at the outside is formed as a carrier and two layer-like heater elements are integrated into the structure;

Figure 1:
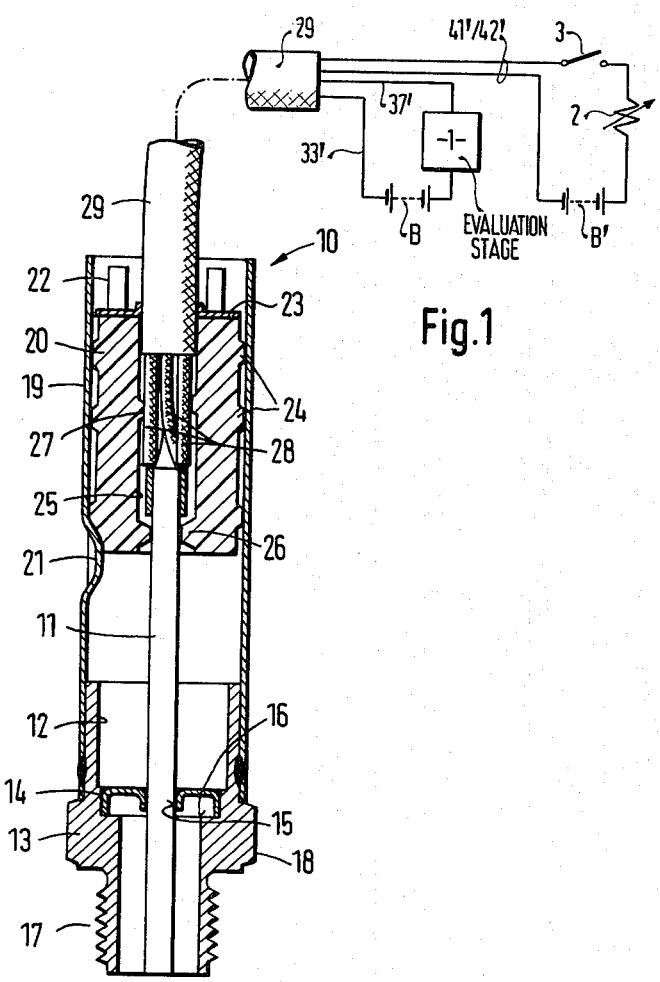
FIG. 1 is a highly schematic longitudinal sectional view through a sensor, shown to an enlarged scale.

The sensor shown in cross section of FIG. 1 is particularly suitable to test exhaust gases emanating from automotive-type internal combustion engines. It operates in the polarographic mode according to the current limiting principle described, for example, in U.S. Pat. No. 3,691,023, Ruka and Panson. The sensor 10 has a heated sensor element 11. A portion of its length is retained in a longitudinal opening 12 of a metal housing 13. A bracket or support element 14 retains the flat plate 11 in position in the housing. The support element 14 is a metal disk having a central opening 15 therein. The outer edge as well as the central opening are formed with flanges extending essentially perpendicularly to the major plane of the disk 14; the outer flanges bear against matching shoulders 16 on the metal housing or socket 13; the inner flanges provide longitudinal guidance to the sensor element 11. The sensor element 11 is additionally secured in a central opening 15 by a solder, for example a glass or other hard solder to provide a secure tight connection between the disk 14 and the sensor element 11. The outer flange of disk 14, which bears against the shoulder 16 in the longitudinal opening 12 of the socket 13 is likewise connected to the socket 13 by means of a solder, braze, or weld connection and securely and sealingly connected thereto. Again, glass or hard solder is preferably used; other connection means may be utilized, for example suitable cements, adhesives, or weld connections. Usually, a single transverse holding element 14 is sufficient to secure and maintain the sensor element 11; if necessary, however, two or more such disks 14 may be used, and may be recommended. The holding disk 14 may be of metal or may be of ceramic; it is preferred to form disk 14 as a metal disk since it is more elastic and thus has better retaining capabilities upon changes in temperature and temperature gradients. If the connection between ceramic and metal portions, or ceramic parts themselves is by means of a solder connection, then the respective ceramic portions should be metalized before soldering at their engaging surfaces.

The metal housing 13 is suitably shaped to insert the sensor in the path of the gases to be tested, for example by screwing the sensor end into a suitably tapped opening in the exhaust pipe from an internal combustion engine. It is threaded at the outside as shown at 17 and formed with a hexagonal outer socket surface 18 so that a wrench can be applied to the sensor element 10. The housing 13 is short and compact to save on materials. A metal sleeve 19 extends the housing 13 outwardly towards the end of sensor element 11 which is remote from the test gas. Housing 13 and the metal sleeve 19 preferably are connected by welding. The metal sleeve 19 has an insulating bushing 20 secured thereto, which seals off the sleeve 19. Bushing 20 is held in position by one or more dimples 21 pressed into the sleeve. One or more tabs 22 punched out of the circumference of the sleeve towards the end and pressed over the bushing 20 provides for strain relief. A washer 23 is interposed between bushing 20 and the end of the sleeve 19 to form a mechanically strong metallic closure and to protect the bushing 20 against mechanical damage. The insulating bushing 20 which, in order to facilitate assembly into the metal sleeve 19, is formed with a plurality of shoulders 24 at its circumference. It has a central bore 25 with a sealing shoulder 26 extending into the bore 25 at the lower portion (FIG. 1) which, additionally, is used to locate the heatable sensor element 11 in position. A second sealing shoulder 27 is positioned internally of the bushing 20 and engages the electrical connections 28 of the connection and sensing line cable 29. The connecting lines 28 include conductors 33', 37' which are connected to a source of voltage B, for example a voltage regulated derivative source from the vehicle battery, and to an evaluation stage 1. Neither the voltage source nor the evaluation stage are the subject matter of the present invention. Cable 29 further includes conductors 41', 42' for connection to the heating system—as will be explained—which are, in turn, connected through a switch 3 and, if desired, an adjustable resistor 2 to a source of electrical power, for example battery B' which can be the battery of the vehicle and can be identical to the primary source of electricity which provides a bias voltage, represented by source B, to conductors 33', 37'.

The sensor element 11 terminates approximately flush with the metal housing 13. It thus does not necessarily require additional protective shields or the like to protect the sensor against particles in the measuring gas which might impinge thereagainst. It is connected to two conductors 33', 37', forming part of the electrical connections 28, in such a manner that both electrodes of the sensor are individually connected to individual conductors and that one of them is not grounded to the metal housing. It is of course possible also to connect one of the output leads of the sensors with the metal housing although, for automotive use, carrying out the sensor electrodes galvanically separate from the remaining electrical system has advantages with respect to noise level of the output signal.

An exploded view of the sensor construction of sensor element 11 of the overall sensor unit 10 is best seen in FIG. 2: An elongated plate-like oxygen ion conductive solid electrolyte body forms the primary element. The plate-like body 30, for automotive applications, may for example have a thickness of about 0.8 mm and a width of about 5 mm. At the terminal portion adjacent the gas to be tested, the solid electrolyte body 30 has on its upper flat side 31 a porous platinum layer of a measuring electrode 32. This measuring electrode 32, which may form the cathode, has a thickness of about 7 $\mu$m. It is connected to, and preferably integral with a conductive strip 33 positioned centrally on the surface 31 and extending to the end portion remote from the sensing end of the solid electrolyte body. The electrode 32, as well as the conductive strip 33, can be applied by any suitable and well known process, for example by printing, by rolling-on, spraying-on, vapor deposition, or the like. The electrode and the connecting strip 33 preferably are of platinum and may have openings formed therein, for example and preferably also in the conductive strip, in the order of about 0.01 mm$^2$. A porous cover 34 which entirely covers the electrode 32 is located above the electrode, protecting the electrode upwardly and extending additionally laterally thereover to encapsulate the electrode. The porous cover 34 has a predetermined diffusion resistance to oxygen molecules. It is applied by pressing on a suitable substance, for example zirconium dioxide, aluminum oxide, magnesium spinel, or the like, and subsequent heating to incandescence. This cover, which can have a thickness of for example about 0.5 mm, is formed with pores having a diameter of less than 1.0 μm. It is made porous in known manner by applying a predetermined quantity under a predetermined pressure and/or providing an additional additive which forms interstices. An additive forming interstices is, for example, carbon which, upon carrying out the above mentioned heating to incandescence, or upon a subsequent sintering process, is removed at that time. The sensing electrode conductive connective strip 33 is protected against the corrosive influence of gases also by a suitable protective layer; in the example shown, this protective function is carried out by the porous cover 34 which is extended to the requisite length and at the terminal ends is relieved so that the conductive strip 33 can be contacted by suitable contacts, or joints (not shown) to the connection leads 28. The openings formed in the measuring electrode 32 and in the associated strip 33 are used to improve the adhesion between the solid electrolyte body and the porous cover 34, that is, to permit direct contact between cover 34 and the body 30.

A reference electrode 36 is located at the lower side of the solid electrolyte body. Its size and material and dimensions essentially correspond to the sensing electrode 32. The electrode 36 also is formed with an extended conductive strip 37. In order to prevent short circuit currents between the electrode conductive strips 33 and 37 when the sensor 10 is in operation, and thereby possibly obtain erroneous measuring output signals, an electrically insulating layer 38 is located between the reference electrode conductive strip 37 and the solid electrolyte body 30. A similar insulating layer could also be applied at the upper side of the solid electrolyte 30 in the region of the conductive strip 33 or the insulation could be placed at the upper side only. The insulating layer 38 may consist, for example, of $ZrO_2$ or aluminum oxide. A layer-like electrical insulator 39, for example $ZrO_2$ or aluminum oxide, is located on the reference electrode 36 and its conductive strip 37. The layer insulator 39 is so arranged and dimensioned that it permits at least lateral access of oxygen-containing sensing gas to the reference electrode 36.

The elements described with reference numerals 30 to 39 form the actual sensor element 11. In addition to the sensor structure, a heating element 40 is placed on the electrical insulator 39, for example similar to a printed circuit. Heating element 40 is an undulating, zig-zag or meander-like conductive strip of platinum, which has a thickness of about 10 μm. It is located essentially in the region of the reference electrode 36 and is connected to conductive strips 41, 42 which form electrical connections thereto and extend to the end portion of the sensor element 11 remote from the sensing gas. The conductive strips 41, 42 extend along the two longitudinal sides of the sensor element 11, so that they are outside of the projected dimension of the reference electrode connector 37. The heating element 40 and the associated connecting strips 41, 42 are covered with a porous protective layer 43 leaving, however, enough space to form a contact connection to the conductive strips 41, 42 at the terminal ends thereof. The protective layer 43 protects the heating element 40 and the conductive strips 41, 42 against the corrosive gases to which the sensor can be exposed, and may consist, for example, of $ZrO_2$ or aluminum oxide.

The sensor element 11 together with the heating element 40 and the protective layer 43 applied thereover form a stacked, laminar package or unit 44 which is sintered together, and which can readily be made economically under mass production conditions by well known processes. Due to the low heat capacity of the sensor unit, it will reach operating temperature rapidly, requiring only little heat energy. Thus, the sensor can be rapidly brought to operating conditions.

Embodiment of FIG. 3: The structure within the bracket 44/1 corresponds to the structure 44 of FIG. 2. The element 45 of FIG. 3 differs from the element 44 of FIG. 2 by the presence of a second heater element 46. Heater element 46 is located on a porous cover 34/1 and, generally, corresponds in its structure and operation to the heater element 40 of FIG. 2. A protective layer 49 is applied to the connecting tracks 47, 48 of the heater element 46 to protect the heater element 46 and the connecting tracks against the corrosive hot gases to be sensed. The terminal end portions of the connecting tracks 47, 48 are left blank to permit making of a connection to a heater supply line. In order to permit access of the gas to the porous cover 34/1, the protective layer 49 is formed with openings 50 which can be shaped as holes or elongated slots. Sensor element 11/1 with the two heating elements 40/1 and 46 has a particularly rapid sensing response since the necessary operating temperature of about 700° C. to obtain useful measuring results from the sensor 10 is reached rapidly. It is thus particularly suitable for use in environments in which the sensor 10 is located comparatively far away from the exhaust manifold or exhaust valves of an engine, and is located, for example, in the exhaust system as such, for example in a Y-junction of two exhaust branches from a V-type engine or an opposed piston engine.

It has been found advantageous to make the sensor elements 11 in multiple parts, particularly in order to improve the flexibility of models and manufacturing steps, and to decrease the reject rate in manufacture.

Embodiment of FIG. 4: A sensor element 11/2 forms the inner portion of a layer-like unit, corresponding essentially to the sensor element 11 of FIG. 2. The solid electrolyte body 30/2 has a porous cover 34/2 and a protective layer 43/2 on the reference electrode 36/2. The second structural element is formed by a first insulator 51 which has approximately the same dimensions as the sensor element 11/2, and may consist, for example, of aluminum oxide which is coated with the heating element 40/2, including the connecting tracks 41/2, 42/2, manufactured in any known and suitable manner. The heating element 40/2 together with the connecting tracks 41/2, 42/2 is made of platinum metal. This unit, together with the heating element 40/2, is rigidly secured to the sensor element protective layer 43/2 in the region of the reference electrode 36/2. An additional protective layer to cover the heating elements 40/2 and the connecting tracks 41/2, 42/2 was omitted since it is necessary only from case to case.

The third structural unit is a second electrical insulator 52 which, similar to the insulator 51, has a heating element 46/2 and associated connecting tracks 47/2, 48/2. It, likewise, may be of aluminum oxide and, together with its heating element 46/2, is applied on the porous cover 34/2 of the sensor element 11/2, being tightly laid thereon. This element, also, may be protected by a further protective cover applied to the heating element 46/2 and the conductive tracks 47/2, 48/2, if necessary. In order to permit the sensing gas to have access to the sensor element 11/2, it is preferred to form the insulator 52 with access openings 53, formed as slots or holes which penetrate in the region of the element 46/2 through the insulator 52 and which terminate directly on the sensor element cover 34/2. The heating element 46/2 is so placed that its windings pass around the openings 53. For some constructions, the openings 53 are not needed if the insulator 52 is sufficiently porous to the sensing gas.

All three units, the sensor 11/2 itself, the heating element support 51 and the heating element support 52, are secured together in the sensor 10 by means of the holding disk 14 (FIG. 1) and the insulating bushing or plug 20. If necessary, however, they can be fixed with respect to each other by projections, dimples and matching recesses, abutments or the like, in order to prevent relative movement and shifting of the subunits.

Embodiment of FIG. 5: The sensor element 11/3 is similar to that of FIG. 4. In contrast to the structure of FIG. 4, however, in which the heating elements 40/2, 46/2 are applied to the side facing the sensor—which is a preferred embodiment since generated heat is rapidly transmitted to the solid electrolyte—the insulators 51/1 and 52/1 of FIG. 5 have the heating elements 40/3, 46/3, respectively, applied to the side remote from the sensing element 11/3. The heating element 40/3, 46/3 and the respective connecting tracks or paths 41/3, 42/3 and 47/3, 48/3 are protected against the corrosive influence of the hot measuring gases and thus are covered with a protective layer 43/3, 49/3, respectively. Openings 53/1 are formed in the insulator 52/1 which fit and match the openings 54 formed in the protective cover 49/3 in order to permit access of measuring gas to the sensing electrode.

The heating elements 11/2 (FIG. 4) and 11/3 (FIG. 5) need not necessarily have an electric insulator 51, 53 or 51/1, 52/1, respectively, on both sides; for some constructions, it may be sufficient if only one insulator has a heating element applied thereto, so that the sensor elements 11/2, 11/3 are heated only from one side, as explained in connection with FIG. 2.

Embodiment of FIG. 6: The sensor element 11/4 is heated only from one side. It differs from the sensor element 11 of FIG. 2 in that, instead of the solid electrolyte plate 30 (FIG. 2), an electric insulator element 39/4 is provided as a substrate or carrier for the unit 44/4 so that a lesser quantity of the relatively expensive solid electrolyte body 30/4 is needed than in the previously described structures. The thickness of the solid electrolyte plate 30/4 thus can be reduced from 0.8 mm (FIG. 2) to about 0.05 mm, that is, more than one order of magnitude. The heating element 40/4 in this construction is applied to the back side of the insulator 39/4. The insulator 39/4, like the insulator 39 (FIG. 2), may be made of aluminum oxide or $ZrO_2$.

Embodiment of FIG. 7: A unitary sensor element 11/5 has two heating elements 40/5, 46/5. An electric insulator plate 51/2 forms the carrier element for the entire unit 44/5, and is positioned at one outside surface of the overall sensing unit.

In this embodiment, a relatively thin plate-like solid electrolyte plate 30/5 may be used, similar to that of solid electrolyte plate 30/4 (FIG. 6). The remaining structure in general corresponds to the arrangement of the elements of sensor element 11/2, see FIG. 4. The sensor element 11/5 is particularly suitable for mass production manufacture.

The porous cover 34 of the unit 44, FIG. 2, must have a predetermined diffusion resistance with respect to oxygen molecules. As explained, it was made by pressing the cover on the measuring electrode 32 or, rather, on the solid electrolyte plate 30 to which the measuring electrode 32 and the conductive track 33 has been applied, with subsequent heating to incandescence. Rather than using this process, the solid electrolyte plate 30/6—see FIGS. 8 and 9—may be applied only at the region adjacent the sensing gas portion of the sensor, in which the solid electrolyte plate is formed with a shallow recess 55. The recess 55 may also be in the shape of a slit with an abutment. The measuring electrode 32/6 extends into this recess or slit-like portion and will be at a level below the surface of the remainder of plate 30/6. This recess or slit-like portion is then filled with a porous covering 34/6. This arrangement results in a highly compacted solid electrolyte zone between the measuring electrodes 32/6 and the counter electrode 36/6 which has a high conductivity with respect to oxygen ions. The connecting track 33/6 which is integral with the measuring electrode 32/6 is then covered with a cover coating 56 which is impervious to oxygen molecules, and may consist, for example, of ceramic glass or similar substance in order to prevent interference with the true measuring signal which may result in erroneous output. The remaining structure of a sensor then can be in accordance with any one of the FIGS. 2–7.

Figure 8:
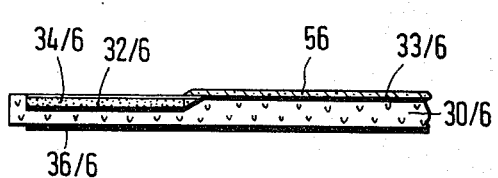
FIG. 8 (on sheet 1 of the drawings) is a longitudinal sectional view through the end portion of the sensor element which is exposed to the test gas, in which the porous cover is located in a recess or pocket of the solid electrolyte plate.
Figure 9:
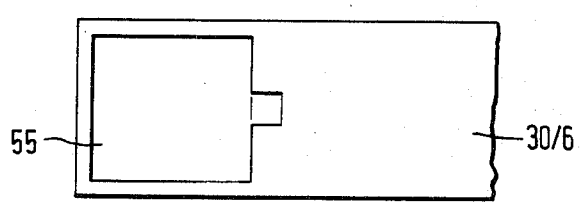
FIG. 9 is a top view of the embodiment of FIG. 8.

A good alternative for the manufacture of the porous cover is the separate manufacture of a plate-like cover and application thereof on the solid electrolyte plate on which the measuring electrode has already been applied, the overall construction then being in accordance with any one of the embodiments of FIGS. 2–7 and/or FIGS. 8 and 9. If the cover as made in FIG. 8 is used, in which a premanufactured cover is located in a recess in the solid electrolyte body, then the lateral gap between the cover and the solid electrolyte body should be sealed, for example with a high temperature melting glass. Separate manufacture of the cover permits excellent control of the predetermined diffusion resistance for oxygen molecules, by selection of the cover substance and/or the pressure upon manufacture of the cover and/or the use of substances which form interstices or voids; additionally, the thickness of the cover can be accurately controlled, for example by subsequent removal of thin surface layers, for example by grinding or other mechanical material removal methods.

Various changes and modifications may be made, and particularly the arrangement of holding and sealing the sensor element 11 within the housing 13 and within the metal sleeve 19 can be changed and varied as desired to meet manufacturing and application requirements. These holding arrangements themselves do not form part of the present invention. Other changes and modifications may also be made, and features described in connection with any one of the embodiments may be used with any of the others, within the scope of the inventive concept.

A suitable heating system (B', 2, 3, 41' 42') is described in U.S. Pat. No. 4,033,170 (Kawamura et al).

We claim:

1. Polarographic electrochemical sensor to determine the oxygen content in gases, particularly in the exhaust gases from an internal combustion engine, comprising
   a plane, elongated plate-like oxygen ion conductive solid electrolyte sensor element body;

first and second gas pervious electrodes located on, and in contact with, respectively, opposite plane surfaces of the body, said electrodes and said body therebetween being exposed to the gases;

a porous cover positioned on one of the electrodes, said cover having a predetermined diffusion resistance to oxygen molecules;

a flat insulating element having at least approximately the same dimensions as said solid electrolyte body and positioned parallel to said body;

a flat layer-like electrical heating element secured on said flat insulating element and positioned closely adjacent to said electrodes and parallel to the plane surfaces of the body;

means for applying an electrical voltage to said electrodes;

means for connecting electrical energy to said heating element, said plane sensor element, said electrodes, said porous cover, said flat insulating element and said flat heating element being assembled in a stacked, laminar package;

a housing retaining said package and permitting access of the gas to a sensing portion thereof;

the solid electrolyte body is formed with a depression or recess beneath one of the electrodes;

one of the electrodes being located at the bottom of the recess and at a level below the remainder of the surface of the body, and wherein the porous cover is fitted within the recess and over the electrode therein and essentially fills the recess or depression and entirely covers the electrode.

2. Sensor according to claim 1, wherein the porous cover is a compacted compressed element of predetermined porosity.

3. Sensor according to claim 1, further including conductive tracks connected to the electrodes and to the heating element, respectively, and extending through said housing to the portion of the body remote from the sensing portion thereof.

4. Sensor according to claim 1, wherein the ends of the conductive tracks form connection terminals to external conductors for connection, respectively, to said means applying an electrical voltage and to the means connecting electrical energy to the heating element, respectively.

5. Sensor according to claim 1, wherein the solid electrolyte body with the electrodes thereon, one insulating element and one electrical heating element, forms a basic sensing element;

and wherein further insulating elements are positioned at the outside plane surfaces of the basic sensing element;

and at least one holding means in the housing securing said elements together.

6. Sensor according to claim 1 wherein electrical insulators are provided, and lying flat against the sensor element the outermost surfaces of said laminar package are electrically insulating;

and having a clamping element securing said electrical insulators and the sensor element together.

7. Sensor according to claim 6, wherein a protective cover is provided, covering the at least one heating element.

8. Sensor according to claim 7, wherein the protective cover is applied to the at least one heating element at the side of the electric insulator facing the basic sensing element.

9. Sensor according to claim 1, wherein the solid electrolyte body with the electrodes thereon, at least one insulating element, and at least one electrical heating element are formed as elongated structures of essentially rectangular shape and of at least approximately similar size to provide an elongated, essentially rectangular package;

and holding means located within a central opening of the housing and retaining said elongated, essentially rectangular package in position in the housing, the holding means being sealingly connected to said elements and plates to seal the package in the housing with the sensing portion thereof projecting beyond the holding means.

10. Sensor according to claim 9, wherein the electrical heating element includes a pair of elongated support plates, one, each, located at either one of the plane flat sides of the solid electrolyte body.

11. Sensor according to claim 1, wherein the electrical insulating element is formed as a plate-like structural support element, and the solid electrolyte plate with one electrode interposed, to be positioned against said insulating plate-like element to be structurally supported thereby.

12. Sensor according to claim 11, wherein the insulating plate-like element comprises at least one of the materials selected from the group consisting of aluminum oxide; $ZrO_2$;

and the solid electrolyte oxygen ion conductive plate has a thickness in the order of about 0.05 mm.

13. Sensor according to claim 1, wherein the flat insulating element comprises an insulating plate.

14. Sensor according to claim 1, wherein the flat insulating element comprises a layer of insulating material.

* * * * *

UNITED STATES PATENT AND TRADEMARK OFFICE
CERTIFICATE OF CORRECTION

PATENT NO. : 4,334,974

DATED : June 15, 1982

INVENTOR(S) : Klaus MULLER et al.

It is certified that error appears in the above—identified patent and that said Letters Patent is hereby corrected as shown below:

Claim 4, line 1 (col. 9, line 44), change "claim 1" to --claim 3--.

Signed and Sealed this

Thirty-first Day of August 1982

[SEAL]

Attest:

Attesting Officer

GERALD J. MOSSINGHOFF

Commissioner of Patents and Trademarks